US012698336B2

(12) United States Patent
Liao et al.

(10) Patent No.: US 12,698,336 B2
(45) Date of Patent: Aug. 4, 2026

(54) ANTI-HUMAN CD73 MONOCLONAL ANTIBODY WITHOUT HOOK EFFECT

(71) Applicant: XINTRUM PHARMACEUTICALS, LTD., Nanjing (CN)

(72) Inventors: Gaoyong Liao, Nanjing (CN); Haijian Ding, Nanjing (CN); Yi Zhang, Nanjing (CN)

(73) Assignee: JIANGSU KANION PHARMACEUTICAL CO., LTD., Liangyungang (CN)

( * ) Notice: Subject to any disclaimer, the term of this patent is extended or adjusted under 35 U.S.C. 154(b) by 664 days.

(21) Appl. No.: 18/031,130

(22) PCT Filed: Apr. 28, 2022

(86) PCT No.: PCT/CN2022/089917
§ 371 (c)(1),
(2) Date: Apr. 10, 2023

(87) PCT Pub. No.: WO2023/206242
PCT Pub. Date: Nov. 2, 2023

(65) Prior Publication Data
US 2024/0368299 A1      Nov. 7, 2024

(51) Int. Cl.
*C07K 16/28*          (2006.01)
*A61K 39/00*          (2006.01)
*A61P 35/00*          (2006.01)

(52) U.S. Cl.
CPC .......... *C07K 16/2896* (2013.01); *A61P 35/00* (2018.01); *A61K 2039/505* (2013.01); *C07K 2317/92* (2013.01)

(58) Field of Classification Search
CPC ............ C07K 16/2896; C07K 2317/92; C07K 2317/76; A61P 35/00; A61K 2039/505
See application file for complete search history.

(56) References Cited

FOREIGN PATENT DOCUMENTS

| | | |
|---|---|---|
| CN | 106852149 A | 6/2017 |
| CN | 110023336 A | 7/2019 |
| CN | 110240654 A | 9/2019 |
| CN | 111434688 A | 7/2020 |
| CN | 112513089 A | 3/2021 |
| CN | 114075289 A | 2/2022 |
| WO | 2021227306 A1 | 11/2021 |

OTHER PUBLICATIONS

Marriuzza et al. The structural basis of antigen-antibody recognition. Ann. Rev. Biophys. Biophys. Chem. 16, 139-159, 1987. (Year: 1987).*
International Search Report on PCT/CN2022/089917.

* cited by examiner

*Primary Examiner* — Elly-Gerald Stoica
(74) *Attorney, Agent, or Firm* — Yong Chen; Lin Sun-Hoffman; Liu Chen & Hoffman LLP

(57)          ABSTRACT

The present invention provides a novel anti-CD73 monoclonal antibody. The antibody has high affinity for human CD73 protein. Both biochemical-level and cell-level experiments show that the antibody is highly effective in inhibiting the enzyme activity of CD73. The in-vivo experiment indicates that the antibody has a significant inhibition effect on tumor cell growth. In particular, the antibody does not have the "hook effect" most prior art antibodies have in connection with inhibition of the enzyme activity of CD73, and is therefore more suitable for clinical use than the prior art antibodies.

5 Claims, 3 Drawing Sheets

Specification includes a Sequence Listing.

SEQUENCE LISTING

```
<160> NUMBER OF SEQ ID NOS: 8

<210> SEQ ID NO 1
<211> LENGTH: 5
<212> TYPE: PRT
<213> ORGANISM: Mus musculus

<400> SEQUENCE: 1

Gly Tyr Thr Met Asn
1               5

<210> SEQ ID NO 2
<211> LENGTH: 17
<212> TYPE: PRT
<213> ORGANISM: Mus musculus

<400> SEQUENCE: 2

Phe Ile Thr Pro Tyr Asn Gly Asp Thr Ile Tyr Asn Gln Lys Phe Lys
1               5                   10                  15

Gly

<210> SEQ ID NO 3
<211> LENGTH: 10
<212> TYPE: PRT
<213> ORGANISM: Mus musculus

<400> SEQUENCE: 3

Glu Gly Tyr Asp Gly Gly Tyr Phe Asp Tyr
1               5                   10

<210> SEQ ID NO 4
<211> LENGTH: 11
<212> TYPE: PRT
<213> ORGANISM: Mus musculus
```

-continued

```
<400> SEQUENCE: 4

Arg Ala Ser Glu Asn Ile Tyr Ser Tyr Leu Ala
1               5                   10

<210> SEQ ID NO 5
<211> LENGTH: 7
<212> TYPE: PRT
<213> ORGANISM: Mus musculus

<400> SEQUENCE: 5

Asn Thr Gln Thr Leu Ala Glu
1               5

<210> SEQ ID NO 6
<211> LENGTH: 10
<212> TYPE: PRT
<213> ORGANISM: Mus musculus

<400> SEQUENCE: 6

Gln His His Tyr Gly Thr Pro Met Tyr Pro
1               5                   10

<210> SEQ ID NO 7
<211> LENGTH: 119
<212> TYPE: PRT
<213> ORGANISM: Mus musculus

<400> SEQUENCE: 7

Glu Val Gln Leu Gln Gln Ser Gly Pro Glu Leu Val Lys Pro Gly Ala
1               5                   10                  15

Ser Met Lys Ile Ser Cys Lys Ala Ser Gly Tyr Ser Phe Thr Gly Tyr
            20                  25                  30

Thr Met Asn Trp Val Lys Gln Ser His Gly Lys Asn Leu Glu Trp Ile
            35                  40                  45

Gly Phe Ile Thr Pro Tyr Asn Gly Asp Thr Ile Tyr Asn Gln Lys Phe
            50                  55                  60

Lys Gly Lys Ala Thr Val Thr Val Asp Lys Ser Ser Ser Thr Ala Tyr
65                  70                  75                  80

Met Asp Leu Leu Ser Leu Thr Ser Glu Asp Ser Ala Val Tyr Tyr Cys
                85                  90                  95

Ala Arg Glu Gly Tyr Asp Gly Gly Tyr Phe Asp Tyr Trp Gly Gln Gly
            100                 105                 110

Thr Thr Leu Thr Val Ser Ser
            115

<210> SEQ ID NO 8
<211> LENGTH: 108
<212> TYPE: PRT
<213> ORGANISM: Mus musculus

<400> SEQUENCE: 8

Asp Ile Gln Met Thr Gln Ser Pro Ala Ser Leu Ser Ala Ser Val Gly
1               5                   10                  15

Glu Thr Val Thr Ile Thr Cys Arg Ala Ser Glu Asn Ile Tyr Ser Tyr
            20                  25                  30

Leu Ala Trp Tyr Gln Gln Lys Gln Gly Lys Ser Pro Gln Leu Leu Val
            35                  40                  45

Tyr Asn Thr Gln Thr Leu Ala Glu Gly Val Pro Ser Arg Phe Ser Gly
            50                  55                  60
```

-continued

```
Ser Gly Ser Gly Thr Gln Phe Ser Leu Lys Ile Asn Ser Leu Gln Pro
65              70                  75                  80

Glu Asp Phe Gly Ser Tyr Tyr Cys Gln His His Tyr Gly Thr Pro Met
                85                  90                  95

Tyr Pro Phe Gly Gly Gly Thr Lys Leu Glu Ile Lys
            100                 105
```

ANTI-HUMAN CD73 MONOCLONAL ANTIBODY WITHOUT HOOK EFFECT

TECHNICAL FIELD

The present invention relates to a genetically engineered antibody and more particularly to an anti-human CD73 monoclonal antibody that has a novel sequence and no hook effect.

DESCRIPTION OF RELATED ART

Ecto-5'-nucleotidase (hereinafter referred to as CD73 for short) is a multifunctional exonuclease that is highly expressed in most solid tumors. CD73 can promote the proliferation of tumor cells and is closely related to the stages, pathological types, and prognoses of tumors.

Most of the existing CD73 antibodies are disadvantaged by the "hook effect", which refers to a phenomenon in which the dose-effectiveness relationship of an antibody against an antigen is changed in such a way that, after reaching a peak value, the therapeutic effect of the antibody increases negatively with the concentration of the antibody. The hook effect makes it difficult to determine the optimal dosages of an antibody for different types of individuals, and this may hinder the antibody from producing the optimal therapeutic effect. One example of such antibodies is MEDI-9447, which is a therapeutic anti-CD73 monoclonal antibody.

In light of the above, the obtainment of an anti-human CD73 antibody that does not have the hook effect may enable the provision of anti-tumor preparations that are more suitable for clinical use than others.

BRIEF SUMMARY OF THE INVENTION

One objective of the present invention is to provide a monoclonal antibody that can inhibit the activity of CD73 effectively and be used to prepare drugs for treating tumor-related diseases.

The present invention provides a novel anti-human CD73 monoclonal antibody that is obtained by screening hybridoma cells derived from BABL/c mice that have been immunized with human CD73 protein. The monoclonal antibody is of the IgG type.

The heavy-chain and light-chain sequences of the anti-human CD73 monoclonal antibody obtained according to the present invention are totally different from those of the existing anti-human CD73 monoclonal antibodies.

The human CD73 protein used in the present invention is a human CD73 protein whose expression was independently conducted by the applicant, with the mice used for the invention being BABL/c mice.

More specifically, the work performed for the present invention as stated above was carried out by the following means:

A. The human CD73 protein was used as an antigen to immunize the BABL/c mice at a dose of 30 μg per mouse. Three weeks after the prime immunization, a boost immunization was performed with the same dosage.

B. The titers of the antibody in the serums of the immunized mice were determined by enzyme-linked immunosorbent assay (ELISA). Once an ideal titer was achieved, an immunological impact was given at a dose of 50 μg.

C. Spleen cells were extracted from the successfully immunized mice and were fused with SP2/0 cells.

When the cells grew into clusters, the titers of the supernatants were determined. After three rounds of subcloning, a positive monoclonal cell strain was obtained.

D. The monoclonal cell strain underwent expansion culture and was then introduced into the mice by intraperitoneal injection so as to produce ascitic fluids. The ascitic fluids were collected and purified to obtain the corresponding antibody.

E. The binding kinetics of the monoclonal antibody was tested by the surface plasmon resonance (SPR) technique.

F. The inhibition effect of the monoclonal antibody on the enzyme activity of CD73 was tested.

G. The tumor inhibition effect of the monoclonal antibody on a transplanted tumor model was tested.

The anti-human CD73 monoclonal antibody obtained according to the present invention was named 7-C10-Ba-C2. The molecular basis of the specificity of this antibody lies mainly in the highly variable complementarity-determining region (CDR)1, CDR2, and CDR3 of each of the heavy chain and the light chain of the antibody. Those CDRs are key areas that bind to an antigen.

The CDR1, CDR2, and CDR3 of the heavy chain and of the light chain of the anti-human CD73 monoclonal antibody obtained according to the present invention are polypeptides whose amino acid sequences are defined as follows:
Antibody 7-C10-Ba-C2:

heavy-chain CDR1: SEQ ID NO. 1; heavy-chain CDR2: SEQ ID NO. 2; heavy-chain CDR3: SEQ ID NO. 3; light-chain CDR1: SEQ ID NO. 4; light-chain CDR2: SEQ ID NO. 5; light-chain CDR3: SEQ ID NO. 6.

As used herein, the term "monoclonal antibody" should be understood as covering any specific binding factor that has the desired specific binding domain and may refer to a monovalent or single-chain antibody, a double-chain antibody, a chimeric antibody, or a derivative, functional equivalent, or homolog of any of the foregoing antibodies, including an antibody fragment and any polypeptide that includes an antigen-binding domain.

One example of such monoclonal antibodies is immunoglobulin G (IgG) in any of its subclasses or subclass allotypes.

While the molecular basis of the specificity of an antibody lies mainly in the highly variable CDR1, CDR2, and CDR3 of each of the heavy chain and the light chain of the antibody, and the CDR sequences should therefore be preserved as much as possible to maintain the optimal binding properties, a change in individual amino acids may still allow the objective of the present invention to be achieved or may even lead to more optimal binding properties, provided that such a change in individual amino acids does not depart from the concept or inventive spirit of the invention.

The region of a heavy or light chain that does not form the highly variable CDR1, CDR2, or CDR3 is defined as a frame region. The frame regions can be substituted by other sequences under the condition that the three-dimensional structure required for binding is not affected.

The beneficial effects of the present invention are as follows:

The anti-human CD73 monoclonal antibody produced according to the present invention has been proved by experiments to have the following outstanding features:

1. The binding kinetics experiment shows that the anti-human CD73 antibody of the present invention has high affinity for human CD73 (see embodiment 2);

2. The biochemical-level and cell-level experiments show that the anti-human CD73 antibody of the present invention is highly effective in inhibiting the enzyme activity of CD73, is different from most of the previously reported CD73 antibodies, and has no hook effect in connection with inhibition of the enzyme activity of CD73 (see embodiment 4); and 3. The animal-based in-vivo pharmacodynamics evaluation experiment shows that the anti-human CD73 antibody of the present invention can significantly inhibit the growth of transplanted tumors in mice reconstituted with human immune cells (see embodiment 5).

Figure 1:
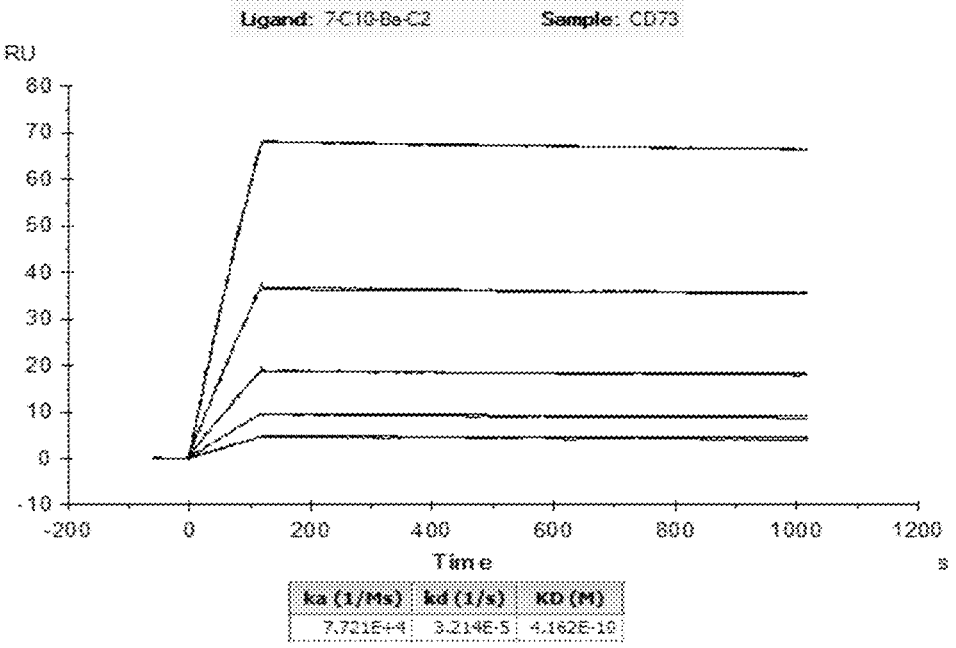
FIG. 1 and FIG. 2 are plots showing the results of the binding kinetics experiment in embodiment 2, with FIG. 1 showing the experimental results of the anti-CD73 monoclonal antibody of the present invention (7-C10-Ba-C2), and FIG. 2 showing the experimental results of the control antibody Contbody (the anti-CD73 monoclonal antibody MEDI-9447 of MedImmune LLC), wherein Ka, Kd, and KD are the binding constant, the dissociation constant, and the affinity constant respectively.

wherein 7-C10-Ba-C2 is the name of the anti-human CD73 monoclonal antibody obtained according to the present invention.

SEQUENCE INFORMATION

SEQ ID NO. 1, SEQ ID NO. 2, and SEQ ID NO. 3 are the CDR1, CDR2, and CDR3 of the heavy-chain variable region of the anti-human CD73 monoclonal antibody 7-C10-Ba-C2 respectively;

SEQ ID NO. 4, SEQ ID NO. 5, and SEQ ID NO. 6 are the CDR1, CDR2, and CDR3 of the light-chain variable region of the anti-human CD73 monoclonal antibody 7-C10-Ba-C2 respectively; and SEQ ID NO. 7 and SEQ ID NO. 8 are the amino acid sequences of the heavy-chain variable region and the light-chain variable region of the anti-human CD73 monoclonal antibody 7-C10-Ba-C2 respectively.

DETAILED DESCRIPTION OF THE INVENTION

To make the objectives, technical solutions, and effects of the present invention clearer and more specific, the invention is described in more detail below by way of the following embodiments. It should be understood, however, that the methods and reagents used in the embodiments serve only to expound the invention but not to limit the scope of the invention.

The present invention provides the heavy-chain and light-chain sequences of a specific anti-human CD73 monoclonal antibody. The monoclonal antibody was expressed in the corresponding monoclonal cell strain obtained by screening hybridoma cells derived from BABL/c mice that had been immunized with a human CD73 protein. The monoclonal antibody is of the IgG type.

The antigen used in the following embodiments is an independently expressed human CD73 protein, with the C terminus of the protein including a 6×His tag.

The immunologic adjuvant employed is the 5-week quick immunoadjuvant (product number: KX0210041) made by Beijing Biodragon Immunotechnologies Co., Ltd. A single boost immunization was conducted 21 days after the prime immunization. Cell fusion was carried out after immunological impact with the antigen was given once.

The fusion method employed is the electrofusion method. The electrofusion equipment used is model ECM2001 of BTX, with the fusion buffer being the cell fusion liquid (product number: 47-0001) provided by BTX.

Once the fused cells grew into clusters, antibody expression in the culture supernatant was tested by ELISA. The ELISA plate was coated with the human CD73 protein or a His protein, wherein the His protein was used to prevent false positive holes due to anti-His.

Subcloning was performed on the positive holes by the limited dilution method. A total of three rounds of subcloning were performed, before a positive monoclonal cell strain was obtained.

An ascitic fluid was prepared with the positive monoclonal cell strain and then purified to obtain the corresponding monoclonal antibody. The monoclonal antibody was subsequently subjected to an affinity test, a CD73 enzyme activity inhibition experiment, and an animal-based pharmacodynamics evaluation.

In the following embodiments, "7-C10-Ba-C2" is the name given to the anti-human CD73 monoclonal antibody provided by the present invention.

Embodiment 1: Immunization with an Antigen, Cell Fusion, Screening for a Positive Clone, and Preparation and Purification of an Ascitic Fluid Antibody Purpose of the Experiment:

To prepare a monoclonal antibody with an independently expressed human CD73 protein serving as the antigen.

Method of the Experiment:

An anti-human CD73 monoclonal antibody was prepared by the hybridoma technology. More specifically, the preparation method is as follows:

Female BABL/c mice that were 4-6 weeks old were each immunized with 30 μg of human CD73 protein.

On the 21$^{st}$ day after the prime immunization, a single boost immunization was given by the same method.

On the 35$^{th}$ day after the prime immunization, blood was collected from the inner canthus, and serum was separated from the collected blood and subjected to an antibody titer test by ELISA.

When the antibody titer reached the required level, 50 μg of human CD73 protein was used as an antigen to make an immunological impact.

Three days after the immunological impact, spleen cells were taken for electrofusion with SP2/0 cells. Once cell clusters were formed, the titers of the anti-human CD73 antibody in the supernatants of the hybridomas were tested by ELISA.

Experimental Results:

After three rounds of subcloning, and by screening according to affinity and the CD73 enzyme activity inhabitation effect, a monoclonal cell strain in which the anti-human CD73 antibody was highly expressed was obtained and was named 7-C10-Ba-C2. The monoclonal cells were expanded and then used to prepare ascetic fluids, which in turn were purified to obtain the antibody for use in the subsequent affinity test, CD73 enzyme activity inhibition experiment, and animal-based pharmacodynamics test.

According to the experimental results, the monoclonal antibody obtained had high affinity, inhibited the enzyme activity of CD73 effectively without producing the hook effect, and had a desirable tumor inhibition effect as demonstrated by the animal-based pharmacodynamics test.

Embodiment 2: Analysis of the Kinetics of the Monoclonal Antibody 7-C10-Ba-C2 in Binding to Recombinant Human CD73

Purpose of the Experiment:

To determine the binding-kinetics constants of the monoclonal antibody 7-C10-Ba-C2 and of the control antibody with the Biacore T200 system.

Reagents and Method:

Mouse Antibody Capture Kit, which is a commercialized reagent kit, was purchased from GE. Anti-mouse Fc IgG was fixated on a CM5 sensor chip by amine coupling in order to capture the antibody under test with the coupled anti-mouse Fc IgG. A series of human CD73 proteins having a predetermined concentration gradient were then injected, before samples were taken and tested with the pH 1.7 glycine-HCl regeneration testing chip that came with the reagent kit.

HBS-EP+ (10 mM HEPES; pH 7.4, 150 mM NaCl; 3 mM EDTA; and 0.05% P20) was used as the running buffer, and the testing temperature was 25° C.

MEDI-9447, which is an anti-CD73 monoclonal antibody of MedImmune LLC, was chosen for use as the control antibody in the experiment and was obtained by synthesis according to the sequence disclosed in its patent specification (US2016/0194407 A1), followed by an expression and purification process. The control antibody obtained was named Contbody.

The binding constant (Ka), the dissociation rate constant (Kd), and the equilibrium constant (KD) were calculated with the Biacore T200 evaluation software by combining the model fitting data at a 1:1 ratio.

Figure 2:
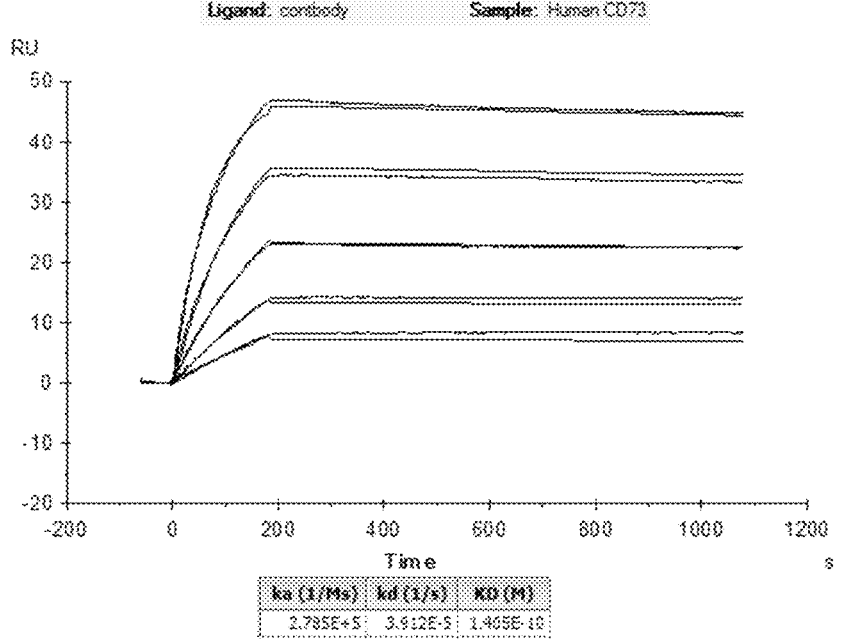

Experimental Results:

The experimental results, or more particularly the affinity data of the antibody of the present invention and of the control antibody, are shown in FIG. 1, FIG. 2, and the following table:

| Antibodies used in the experiment | Ka (1/Ms) | Kd (1/s) | KD (M) |
|---|---|---|---|
| 7-C10-Ba-C2 (antibody of the present invention) | $7.721 \times 10^4$ | $3.214 \times 10^{-5}$ | $4.162 \times 10^{-10}$ |
| MEDI-9447 (control antibody) | $2.785 \times 10^5$ | $3.912 \times 10^{-5}$ | $1.405 \times 10^{-10}$ |

The experimental results show that the monoclonal antibody 7-C10-Ba-C2 had high affinity for the recombinant human CD73, and that the affinity of 7-C10-Ba-C2 was equivalent to that of the control antibody.

Conclusion of the Experiment:

The monoclonal antibody 7-C10-Ba-C2 obtained according to the present invention had high affinity for human CD73.

Embodiment 3: Inhibition of the Enzyme Activity of CD73 by the Monoclonal Antibody 7-C10-Ba-C2

Purpose of the Experiment:

To perform a biochemical-level test and a cell-level test on the ability of the monoclonal antibody 7-C10-Ba-C2 to inhibit the enzyme activity of CD73.

Methods of the Experiment:

1. Biochemical Method

The monoclonal antibody 7-C10-Ba-C2 and the control antibody MEDI-9447 (Contbody) were added separately to the holes of a blank 96-hole plate at an appropriate concentration gradient, and each hole was subsequently added with CD73 protein until the final CD73 protein concentration was 0.25 μg/mL. After incubation at 37° C. for 15 min, AMP and ATP were added separately until their final concentrations were 500 μmol/L and 100 μmol/L respectively. After further incubation at 37° C. for 30 min, each hole was added with the same volume of Cell titer Glo.

The signal values of each hole were determined with a microplate reader by the chemiluminescence method, and the data obtained was subjected to further calculation and processing.

2. Cell-Based Method

The monoclonal antibody 7-C10-Ba-C2 and the control antibody MEDI-9447 (Contbody) were added separately to the holes of a 96-hole plate at an appropriate concentration gradient. A549 cells were digested, resuspended, and counted, and then each hole was inoculated with the A549 cells at a density of $1 \times 10^5$ cells/hole. After incubation in a carbon dioxide incubator for 15 min, each hole was added with AMP until the final AMP concentration reached 500 μmol/L. After further incubation in the carbon dioxide incubator for 24 h, the 96-hole plate was taken out of the incubator and centrifuged at 1000 rpm for 5 min, and 50 μL of supernatant was taken from each hole and added to the corresponding hole of a new blank 96-hole plate. Each hole of the new plate was then added with an ATP solution until the finial ATP concentration was 100 μmol/L, and each hole was subsequently added with the same volume of Cell titer Glo.

The signal values of each hole were determined with a microplate reader by the chemiluminescence method, and the data obtained was subjected to further calculation and processing.

Figure 3:
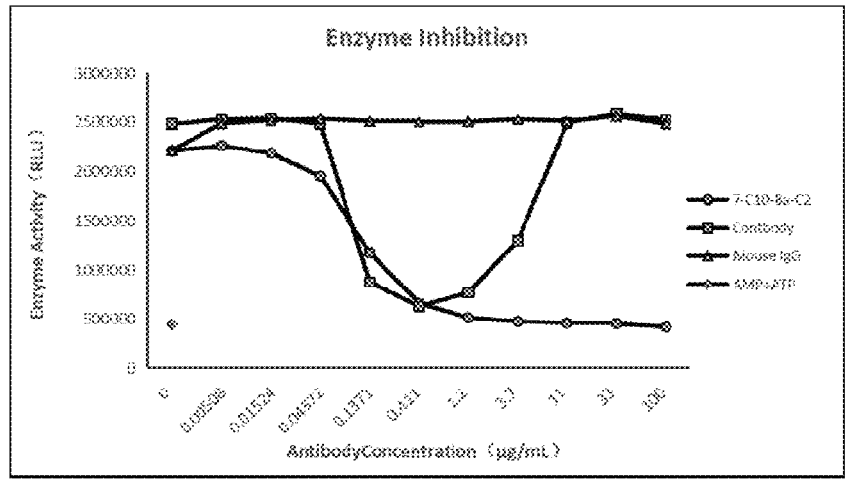
FIG. 3 is a plot showing the results of the biochemical-level experiment in embodiment 3 on the inhibition effect of the monoclonal antibody 7-C10-Ba-C2 on the enzyme activity of CD73.
Figure 4:
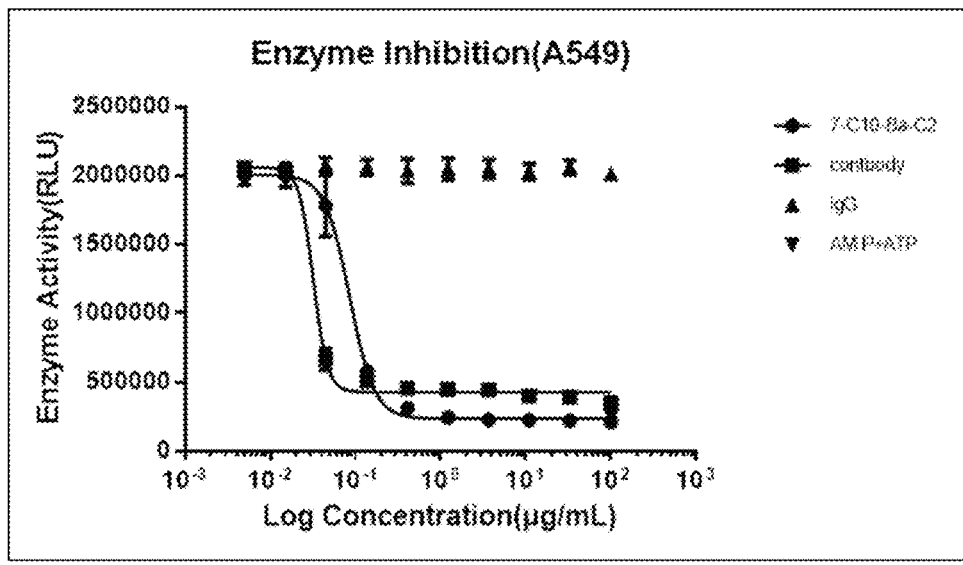
FIG. 4 is a plot showing the results of the cell (A549)-level experiment in embodiment 3 on the inhibition effect of the monoclonal antibody 7-C10-Ba-C2 on the enzyme activity of CD73.

Experimental results: See FIG. 3 and FIG. 4.

The inhibition effects of the antibodies on the enzyme activity of CD73 are summarized in the following table, in which the control antibody is MEDI-9447 (Contbody):

| Antibodies used in the experiment | EC50 (μg/mL) | |
|---|---|---|
| | Biochemical level | Cell level |
| 7-C10-Ba-C2 (antibody of the present invention) | 0.1064 | 0.08544 |
| MEDI-9447 (control antibody) | 0.08964 | 0.03203 |

The inhibition effect of 7-C10-Ba-C2 on the enzyme activity of CD73 was equivalent to that of the control antibody MEDI-9447 (Contbody) on both the biochemical level and the cell level. The enzyme activity inhibition effect of MEDI-9447 was gradually reduced after the concentration of MEDI-9447 exceeded a certain value; as a result, the enzyme activity curve is in the shape of a hook (the hook effect). In contrast to the control antibody MEDI-9447, 7-C10-Ba-C2 maintained its inhibition effect on the enzyme activity of CD73 when the concentration of 7-C10-Ba-C2 was continuously increased, so no hook effect was observed.

Conclusion of the Experiment:

Both the biochemical-level and the cell-level experiments show that the anti-CD73 monoclonal antibody obtained according to the present invention was highly effective in inhibiting the enzyme activity of CD73.

Embodiment 4: Animal-Based Pharmacodynamics Evaluation of the Monoclonal Antibody 7-C10-Ba-C2

Purpose of the experiment: To test the inhibition effect of the monoclonal antibody 7-C10-Ba-C2 on the growth of tumor cells by conducting an in-vivo experiment.

Method of the Experiment:

Ninety B-NDG mice were used. The mice received adaptive feeding for at least one week.

A375 cells were cultured. Subculturing was performed every other day. The cells were eventually collected, and phosphate-buffered saline (PBS) was added to adjust the cell density to $5 \times 10^7$/mL. Each mouse was inoculated with 0.1 mL of the cell suspension by subcutaneous injection into the right shoulder.

About 10 days after the inoculation, mice with a tumor volume ranging from 20 to 30 mm³ were divided into 3 groups, each including 10 mice.

Peripheral blood mononuclear cells (PBMCs) were resuscitated on the day the mice were grouped, and PBS was added to the PBMCs to adjust the cell density to 25 million/mL. Each mouse was intravenously injected with 200 μL of the PBMC solution (5 million PBMCs) and then medicated through intravenous injection. After that, the tumor volumes were measured twice a week. The drug was administered at the frequency of Q3D for a total of 10 times.

A tumor growth curve was plotted for each group, with the vertical axis representing tumor volume, and the horizontal axis representing the drug administration time. One-way ANOVA analysis was performed on each medicated group and the control group in order to compare, and find the differences between, the groups (*: $p<0.05$; : $p<0.01$; *: $p<0.001$).

Figure 5:
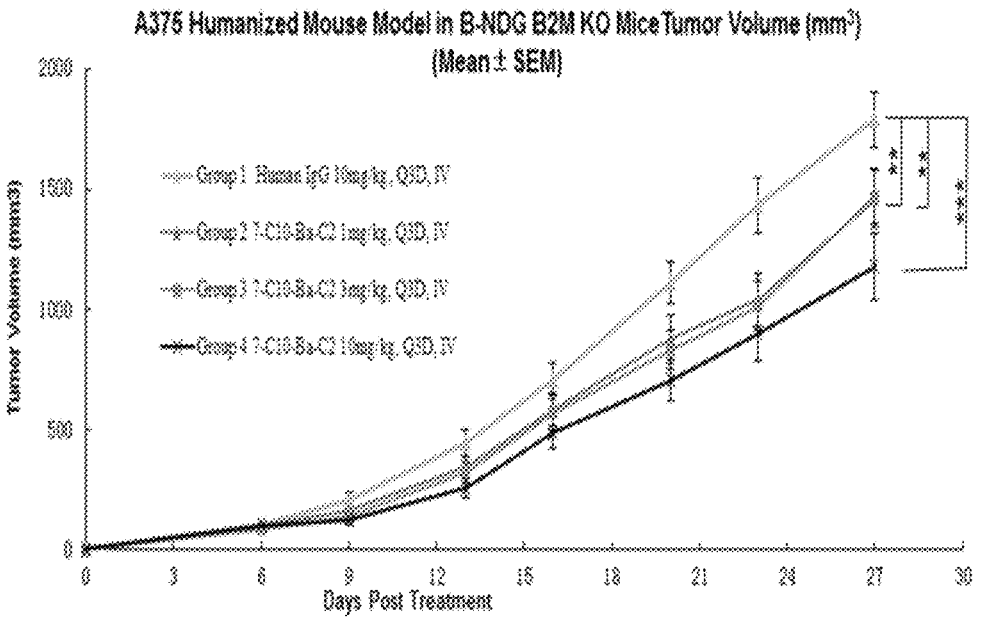
FIG. 5 is a plot showing the results of the animal-based pharmacodynamics evaluation experiment in embodiment 4 on the monoclonal antibody 7-C10-Ba-C2.

Experimental results: See FIG. 5. The experimental results show that, compared with the control-group IgG, the monoclonal antibody 7-C10-Ba-C2 had a significant inhibition effect on the growth of tumor cells.

Conclusion of the Experiment:

The anti-CD73 monoclonal antibody 7-C10-Ba-C2 of the present invention had a significant inhibition effect on the growth of tumor cells.

---

The invention claimed is:

1. An anti-human CD73 monoclonal antibody, comprising: a heavy-chain variable region with complementarity-determining region (CDR) 1, CDR2, and CDR3 that are polypeptides having the amino acid sequences of SEQ ID NO:1, SEQ ID NO:2, and SEQ ID NO:3, respectively; and a light-chain variable region with CDR1, CDR2, and CDR3 that are polypeptides having the amino acid sequences of SEQ ID NO:4, SEQ ID NO:5, and SEQ ID NO: 6, respectively.

2. A drug for treating non-small cell lung cancer or melanoma, comprising the monoclonal antibody of claim 1.

3. A CD73 enzyme activity inhibitor, comprising the monoclonal antibody of claim 1.

4. A method of treating melanoma in a subject, comprising: administering a therapeutically effective amount of the anti-human CD73 monoclonal antibody of claim 1 to the subject.

5. A method of treating non-small cell lung cancer in a subject, comprising: administering a therapeutically effective amount of the anti-human CD73 monoclonal antibody of claim 4 to the subject.

* * * * *